(12) United States Patent
Boettcher et al.

(10) Patent No.: US 9,326,502 B2
(45) Date of Patent: May 3, 2016

(54) STABILIZATION OF COMPOUNDS CONTAINING IODINE HAVING POLYMERS COMPRISING NITROGEN

(71) Applicant: LANXESS Deutschland GmbH, Cologne (DE)

(72) Inventors: Andreas Boettcher, Cologne (DE); Hermann Uhr, Leverkusen (DE); Peter Spetmann, Leverkusen (DE); Thomas Jaetsch, Cologne (DE); Joerg Fuehr, Krefeld (DE)

(73) Assignee: LANXESS Deutschland GmbH, Cologne (DE)

( * ) Notice: Subject to any disclaimer, the term of this patent is extended or adjusted under 35 U.S.C. 154(b) by 26 days.

(21) Appl. No.: 14/354,035

(22) PCT Filed: Nov. 15, 2012

(86) PCT No.: PCT/EP2012/072760
§ 371 (c)(1),
(2) Date: Apr. 24, 2014

(87) PCT Pub. No.: WO2013/072427
PCT Pub. Date: Mar. 23, 2013

(65) Prior Publication Data
US 2014/0303277 A1    Oct. 9, 2014

(30) Foreign Application Priority Data
Nov. 16, 2011   (EP) ..................................... 11189405

(51) Int. Cl.
| | |
|---|---|
| C09D 5/16 | (2006.01) |
| A01N 25/22 | (2006.01) |
| A01N 47/12 | (2006.01) |
| C08G 73/02 | (2006.01) |
| C08L 79/02 | (2006.01) |
| C09D 167/08 | (2006.01) |
| C09D 5/14 | (2006.01) |

(52) U.S. Cl.
CPC ................ *A01N 25/22* (2013.01); *A01N 47/12* (2013.01); *C08G 73/0206* (2013.01); *C08G 73/0213* (2013.01); *C08L 79/02* (2013.01); *C09D 5/14* (2013.01); *C09D 167/08* (2013.01)

(58) Field of Classification Search
CPC ... A01N 25/22; A01N 47/12; C08G 73/0206; C08G 73/0213; C08L 79/02; C09D 167/08; C09D 5/14
See application file for complete search history.

(56) References Cited

U.S. PATENT DOCUMENTS

| | | | |
|---|---|---|---|
| 3,225,013 A | 12/1965 | Fram | |
| 3,350,340 A * | 10/1967 | Soenksen ........... | C08G 73/0213 162/168.2 |
| 3,630,942 A * | 12/1971 | Soldano et al. ........ | B01D 53/70 252/184 |
| 4,276,211 A | 6/1981 | Singer et al. | |
| 4,297,258 A | 10/1981 | Long, Jr. | |
| 4,490,505 A | 12/1984 | Pendergrass, Jr. | |
| 4,552,885 A | 11/1985 | Gabriele et al. | |
| 4,605,698 A | 8/1986 | Briden | |
| 5,534,391 A | 7/1996 | Wang | |
| 6,472,424 B1 | 10/2002 | Gaglani et al. | |
| 7,182,789 B2 | 2/2007 | Decker et al. | |
| 7,943,644 B2 | 5/2011 | Uhr et al. | |
| 8,921,451 B2 | 12/2014 | Bottcher et al. | |
| 2008/0215026 A1 * | 9/2008 | Schornick ............... | A61L 15/60 604/369 |
| 2009/0036555 A1 | 2/2009 | Uhr | |
| 2009/0192219 A1 | 7/2009 | Uhr et al. | |
| 2010/0260691 A1 | 10/2010 | Narayanan et al. | |
| 2012/0208918 A1 * | 8/2012 | Bottcher et al. ............... | 523/122 |

FOREIGN PATENT DOCUMENTS

| | | |
|---|---|---|
| EP | 2236033 A1 * | 10/2010 |
| JP | 2004/331606 A | 11/2004 |
| WO | 97/24390 A | 7/1997 |
| WO | 98/22543 | 5/1998 |
| WO | 99/29176 A | 6/1999 |
| WO | 00/16628 A | 3/2000 |
| WO | 2010/142790 A1 | 12/2010 |
| WO | 2010/0142795 A | 12/2010 |
| WO | 2011/000794 A1 | 1/2011 |

OTHER PUBLICATIONS

Static Light Scattering of Polystyrene Reference Materials: Round Robin Test, U.Just, B.Werthmann International Journal of Polymer Analysis and Characterization, 1999 vol. 5, pp. 195-207.
EP Search Report in corresponding Application No. 11189405 dated May 21, 2012 (3 pages).

* cited by examiner

*Primary Examiner* — Kriellion Sanders

(57) ABSTRACT

The invention relates to the production of nitrogen containing polymers from aziridines, to the use of these nitrogen containing polymers for stabilizing iodine containing compounds, to compositions comprising at least the nitrogen containing polymers and also iodine containing compounds, and to the use of these compositions as biocides and/or for controlling microorganisms.

17 Claims, No Drawings

STABILIZATION OF COMPOUNDS CONTAINING IODINE HAVING POLYMERS COMPRISING NITROGEN

This application is a 371 National Stage Application of PCT/EP2012/072760 filed Nov. 15, 2012, which claims the benefit of EP 11189405.1 filed Nov. 16, 2011. The disclosure of the prior applications is hereby incorporated by reference herein in its entirety.

The invention relates to the production of nitrogen containing polymers from aziridines, to the use of these nitrogen containing polymers for stabilizing iodine containing compounds, to compositions comprising at least the nitrogen containing polymers and also iodine containing compounds, and to the use of these compositions as biocides and/or for controlling microorganisms.

Iodine containing biocides are used for protecting industrial materials such as coating materials, for example, from infestation, decomposition, destruction and visual alteration by fungi, bacteria and algae. Furthermore, iodine containing biocides, both alone and in combination with biocides from other classes of active ingredient, are used as components of biocidally active materials protection compositions such as wood preservatives, for example. Besides iodoalkynyl compounds, active ingredients are also used here in which one or more iodine atoms are bonded to $sp^2$-hybridized carbon atoms of olefinic double bonds, or else to $sp^3$-hybridized carbon atoms.

A behaviour common to many iodine containing biocides is that on exposure to light, even as they are or as a component of an industrial material, they undergo decomposition accompanied by yellowing, and this massively impairs both the biocidal armoury and the tactile qualities of the material to be protected.

Many iodine containing biocides, especially iodoalkynyl compounds, are destroyed with particular rapidity by transition metal compounds. This fact prevents the use of iodine containing biocides, such as more particularly iodoalkynyl compounds, in solvent-based coating materials, such as paints, varnishes and stains, or in biocidal preservatives, such as wood preservative primers, wood preservative impregnation systems and wood preservative stains, since these alkyd resin-based coating and preservation systems typically comprise transition metal compounds. The transition metal compounds such as octoates of cobalt, of lead, of manganese and of vanadium, for example, function here as dryers (siccatives) of the alkyd resin-containing binder system. Furthermore, transition metal compounds are also used as colour-imparting pigments, and have destructive properties comparable with those of the siccatives.

Besides the siccatives there are a range of further constituents in the aforementioned solvent-based systems that lead in different intensities to the degradation of iodine containing biocides. Whereas with the solvents commonly used the destabilizing effect is still relatively weakly pronounced, the other customary components of a paint formulation, such as in-process additives, plasticizers, colour pigments, anti-steeling agents, thixotropic agents, corrosion inhibitors, anti-skinning agents and binders, for example, exhibit a more or less strongly pronounced destabilizing effect.

As well as in the above-described solvent-based systems, the use of iodine containing biocides in certain water-based industrial materials also presents problems. Where, for example, the filming and film curing of a water-based coating material is based on oxidative crosslinking of water-soluble or emulsified alkyd resins, transition metal compounds are employed as siccatives in these systems as well, with a consequent accompanying destruction of the iodine containing biocides.

The prior art has disclosed techniques for preventing the breakdown of iodopropargyl compounds in transition metal-containing, solvent-based paints comprising alkyd resin, and thereby stabilizing them. Thus, for example, the addition of chelating reagents (WO 98/22543 A1 organic epoxides (WO 00/16628 A, U.S. Pat. No. 4,276,211, U.S. Pat. No. 4,297, 258) optionally in conjunction with UV absorbers (WO 99/29176 A) or benzylidene-camphor derivatives (U.S. Pat. No. 6,472,424), tetraalkylpiperidine compounds and/or UV absorbers (EP 0 083 308 A), 2-(2-hydroxyphenyl)benzotriazoles (WO 2007/028527 A) or azole compounds (WO 2007/101549 A) is known.

The action of the abovementioned stabilizers, however, is not always adequate and is hampered by performance disadvantages. For instance, in particular, drying times of paints are significantly prolonged, this being in many cases unacceptable to the user. Moreover, the inhibition of discolouration is not always sufficient.

EP 2 236 033 A describes stabilization by means of stabilizers containing aziridine groups. In this way, however, it is not possible to produce storage-stable concentrates of iodine containing biocides.

By applying aziridines or other nitrogen containing compounds to inorganic carrier materials, such as silicas (WO2010/142790 A), for example, it is possible to obtain good stabilizers, but the requisite spray drying makes their production very energy-intensive.

It is also known that iodine containing biocides can be protected from attack by destabilizing influences in a polymer preparation (WO 2011/000794 A). At the same time, however, the activity is restricted to an extent such that the necessary application rate becomes uneconomically high.

The object, therefore, was to provide compositions which allow effective stabilization of iodine containing compounds, are easy to produce, and cause as little disruption as possible in their application, for example, in coating materials.

It has now been found that nitrogen containing polymers are suitable for effectively protecting iodine containing compounds, especially in (organic) solvent-based and water-based systems, against both chemical and light induced degradation, and hence are able to prevent colour changes and loss of action.

The invention accordingly relates to the use of nitrogen containing polymers for stabilizing iodine containing compounds and also to a method for stabilizing iodine containing compounds by contacting them with nitrogen containing polymers.

Stabilization in the context of the invention means the protection of iodine containing compounds against chemical and/or light induced degradation.

Iodine containing compounds are, for example, iodoalkynyl compounds and also compounds in which one or more iodine atoms are bonded to $sp^2$-hybridized carbon atoms of olefinic double bonds, or to $sp^3$-hybridized carbon atoms. Such compounds preferably exhibit biocidal action.

Examples of iodine containing compounds with biocidal activity are N—($C_1$-$C_{12}$)-alkyl-iodotetrazoles, N—($C_6$-$C_{15}$)-aryl-iodotetrazoles, N—($C_6$-$C_{15}$)-arylalkyl-iodotetrazoles, diiodomethyl p-tolyl sulphone, diiodomethyl p-chlorophenyl sulphone, 3-bromo-2,3-diiodo-2-propenyl alcohol, 2,3,3-triiodoallyl alcohol, 4-chloro-2-(2-chloro-2-methylpropyl)-5-[(6-iodo-3-pyridinyl)methoxy]-3(2H)-pyridazinone (CAS RN: 120955-77-3), iodofenphos, 3-iodo-2-propynyl 2,4,5-trichlorophenyl ether, 3-iodo-2-propynyl 4-chlorophenyl formal (IPCF), N-iodopropargyloxycarbonyl-alanine, N-iodopropargyloxycarbonyl-alanine ethyl ester, 3-(3-iodopropargyl)benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl) hexyl dicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl-carbamic ester (IPC), 3-bromo-2,3-diiodo-2-propenyl ethylcarbamate, 3-iodo-2-propynyl n-hexylcarbamate and 3-iodo-2-propynyl cyclohexylcarbamate.

Preferred iodine containing compounds with biocidal activity are 3-iodo-2-propynyl 2,4,5-trichlorophenyl ether, 3-iodo-2-propynyl 4-chlorophenyl formal (IPCF), N-iodopropargyloxycarbonyl-alanine, N-iodopropargyloxycarbonyl-alanine ethyl ester, 3-(3-iodopropargyl)benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl)hexyl dicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl-carbamic ester (IPC), 3-bromo-2,3-diiodo-2-propenyl ethylcarbamate, 3-iodo-2-propynyl n-hexylcarbamate and 3-iodo-2-propynyl cyclohexylcarbamate.

Particularly preferred iodine containing compounds with biocidal activity are 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl)hexyl dicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl-carbamic ester (IPC), 3-bromo-2,3-diiodo-2-propenyl ethylcarbamate, 3-iodo-2-propynyl n-hexylcarbamate and 3-iodo-2-propynyl cyclohexylcarbamate, with 3-iodo-2-propynyl butylcarbamate (IPBC) being even further preferred.

The nitrogen containing polymers possess preferably a weight-average molecular weight of more than 1000 g/mol, preferably 2000 to 100,000 g/mol and more preferably 3000 to 60,000 g/mol determined by gel permeation chromatography against polystyrene standard (unless otherwise specified: polystyrene/PSS Polymer kit).

The nitrogen containing polymers preferably have a nitrogen content of 1 to 20 wt %, preferably 2 to 15 wt % N, and more preferably 5 to 12 wt % N determined by elemental analysis. Particularly suitable nitrogen containing polymers are those having structural units which derive from aziridines.

Nitrogen containing polymers are preferably polymers obtainable by reaction of aziridines in the presence of water.

In the reaction of aziridines in the presence of water, the aziridine ring can be opened by nucleophilic reaction with water, to form a beta-amino alcohol. The amino group itself may then, as a strong nucleophile, bring about the nucleophilic ring opening of a further aziridine ring, to form a dimer containing a beta-aminoamine function, which is able in turn to react further to form higher polymers.

Preferred nitrogen containing polymers, therefore, are those possessing at least one, preferably two or more, beta-aminoamine functions.

Particularly preferred nitrogen containing polymers are those which are obtainable by reaction in the presence of water of aziridines which contain one or more unsubstituted or substituted aziridine groups.

Preferred are aziridine compounds of the formula (I)

where
$R^1$ is hydrogen, alkyl or cycloalkyl, each of which is unsubstituted or substituted and/or mono- or polyethylenically unsaturated, or in each case substituted or unsubstituted fullerenyl, aryl, alkoxy, alkoxycarbonyl, arylcarbonyl or alkanoyl,
$R^2$, $R^3$, $R^4$ and $R^5$ independently of one another have the same definition as $R^1$ and additionally independently are halogen, hydroxyl, carboxyl, alkylsulphonyl, arylsulphonyl, nitrile, isonitrile, and
$R^2$ and $R^4$ or $R^1$ and $R^5$, together with the carbon atoms to which they are attached, form a 5- to 10-membered carbocyclic ring which is unsubstituted or substituted and/or mono- or polyethylenically unsaturated.

Monofunctional aziridines of the formula (I) that are contemplated are, for example, those in which $R^2$ and $R^4$ or $R^3$ and $R^5$, together with the carbon atoms to which they are attached, form a 5- to 10-membered carbocyclic ring which is unsubstituted or substituted and/or mono- or polyethylenically unsaturated.

These are, more particularly, those of the formula (II)

where the carbocyclic ring is unsubstituted or substituted by one or more substituents selected from the group consisting of halogen, hydroxyl, oxo, carboxyl, alkylsulphonyl, arylsulphonyl, nitrile, isonitrile, alkyl or cycloalkyl, each of which is unsubstituted or substituted and/or mono- or polyethylenically unsaturated, or substituted or unsubstituted fullerenyl, aryl, alkoxy, alkoxycarbonyl or alkanoyl, and
n is a number from 0 to 6, preferably from 0 to 1.

Likewise preferred are those monofunctional aziridine compounds of the formula (I) in which $R^1$ is a radical of the formula

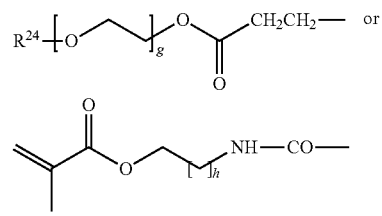

in which $R^{24}$ is —H or alkyl, preferably —H, —CH$_3$, —C$_2$H$_5$, more preferably —CH$_3$, —C$_2$H$_5$, g is a number from 1 to 4, preferably 1 to 3, more preferably 1 to 2, h is a number from 1 to 11, preferably 1 to 5 and more preferably 1 to 3, and the remaining radicals have the above definition.

More particular preference is given to those compounds of the formula (I) which conform to the compound of the formula (III) or (IV)

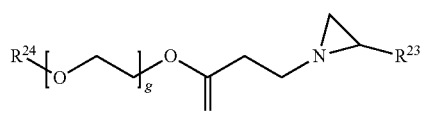
(III)

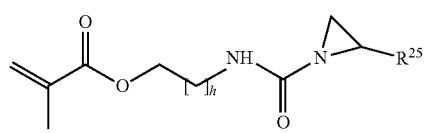
(IV)

where $R^{23}$ is —H or alkyl, preferably —H or —CH$_3$, more preferably —CH$_3$, $R^{25}$ is —H or alkyl, preferably —H or —CH$_3$, more preferably —CH$_3$, and the remaining radicals have the above definition.

Particularly preferred aziridines are those having two or more aziridine functions. Examples include compounds of the formula (V)

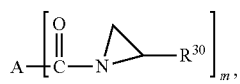
(V)

in which

A is an m-valent aliphatic, cycloaliphatic or aromatic radical, which is optionally substituted, m is a number from 2 to 5, more particularly 2 to 3, and $R^{30}$ for each m unit is in each case independently hydrogen or C$_1$-C$_4$ alkyl, more particularly CH$_3$ or CH$_2$CH$_3$.

Where m is 2, A is preferably C$_2$-C$_{10}$ alkylene, more particularly

—(CH$_2$)$_6$—, —C(CH$_3$)$_2$CH$_2$C(CH$_3$)$_2$CH$_2$— or

—C(CH$_3$)$_2$CH$_2$CH(CH$_3$)CH$_2$— or is a phenylene, more particularly the divalent radical of the formula

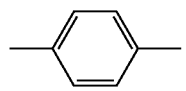

If m is 3, A is preferably the trivalent radical of the formula

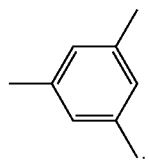

Preferred compounds of the formula (V) are those conforming to the formulae (Va)-(Vd).

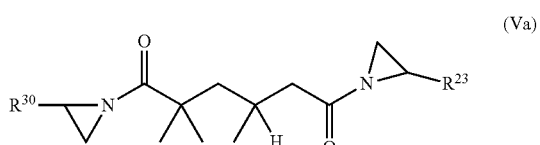
(Va)

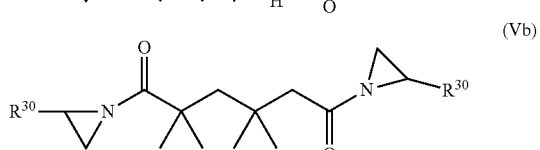
(Vb)

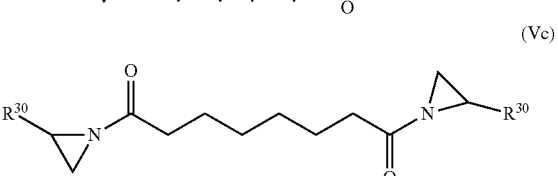
(Vc)

(Vd)

Likewise preferred as polyfunctional aziridine compounds are Michael adducts of optionally substituted ethylenimine with esters of polyhydric alcohols with α,β-unsaturated carboxylic acids and the adducts of optionally substituted ethylenimine with polyisocyanate.

Suitable alcohol components are, for example, trimethylolpropane, neopentyl glycol, glycerol, pentaerythritol, 4,4'-isopropylidenediphenol and 4,4'-methylenediphenol. Examples of suitable α,β-unsaturated carboxylic acids include acrylic acid and methacrylic acid, crotonic acid and cinnamic acid.

With particular preference the composition of the invention comprises acrylic esters.

The corresponding polyhydric alcohols of the α,β-unsaturated carboxylic esters may optionally be alcohols which have been extended on some or all of their OH functions in some cases completely with alkylene oxides, singly or multiply. These may be, for example, the aforementioned alcohols extended singly or multiply with alkylene oxides. In this respect, reference is also made to U.S. Pat. No. 4,605,698, the disclosure content of which is included by reference in the present invention. Alkylene oxides which are particularly suitable in accordance with the invention are ethylene oxide and propylene oxide.

Examples of polyisocyanates suitable for reaction with optionally substituted ethylenimine are those specified at page 4 lines 33-35 of WO 2004/050617 A.

Examples of aziridines that are suitable in accordance with the invention are those specified at page 3 lines 29-34 of WO 2004/050617 A.

Preference is likewise given to those aziridines of the kind described, for example, in U.S. Pat. No. 3,225,013 (Fram), U.S. Pat. No. 4,490,505 (Pendergrass) and U.S. Pat. No. 5,534,391 (Wang).

Likewise preferred are those aziridines of the formula (I) which possess at least three aziridine groups, such as, for example, trimethylolpropane tris[3-(1-aziridinyl)propionate], trimethylolpropane tris[3-(2-methyl-1-aziridinyl)propionate], trimethylolpropane tris[2-aziridinylbutyrate], tris(1-aziridinyl)-phosphine oxide, tris(2-methyl-1-aziridinyl)phosphine oxide, pentaerythritol tris[3-(1-aziridinyl)propionate] and pentaerythritol tetrakis[3-(1-aziridinyl)propionate].

Of these, preference is given particularly to trimethylolpropane tris[3-(1-aziridinyl)propionate], trimethylolpropane tris[3-(2-methyl-1-aziridinyl)propionate], trimethylolpropane tris[2-aziridinylbutyrate], pentaerythritol tris-[3-(1-aziridinyl)propionate] and pentaerythritol tetrakis[3-(1-aziridinyl)propionate].

Particularly preferred are trimethylolpropane tris[3-(1-aziridinyl)propionate], trimethylolpropane tris[3-(2-methyl-1-aziridinyl)propionate] and pentaerythritol tetrakis-[3-(1-aziridinyl)propionate].

Likewise preferred are polyfunctional aziridines of the formula (VI)

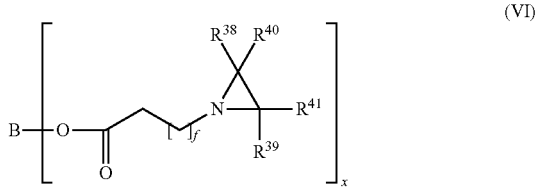

(VI)

in which

B is the radical of an aliphatic polyol which contains at least x OH functions, where x OH functions are substituted by the radical of the above brackets, f is a number from 0 to 6, more particularly from 1 to 3, x is a number greater than or equal to 2, and more particularly is 2 to 100 000, and $R^{38}$ and $R^{39}$ or $R^{40}$ and $R^{41}$, together with the carbon atoms to which they are attached, form a 5- to 10-membered carbocyclic ring which is unsubstituted or substituted and/or mono- or polyethylenically unsaturated.

With particular preference B is the radical of a polyvinyl alcohol. Particularly preferred aziridines of the formula (VI) are those in which x is 3 or 4 and B is a trebly or quadruply OH-functional polyol.

Particularly preferred aziridines of the formula (VI) are those conforming to the formulae (VIa)-(VIc)

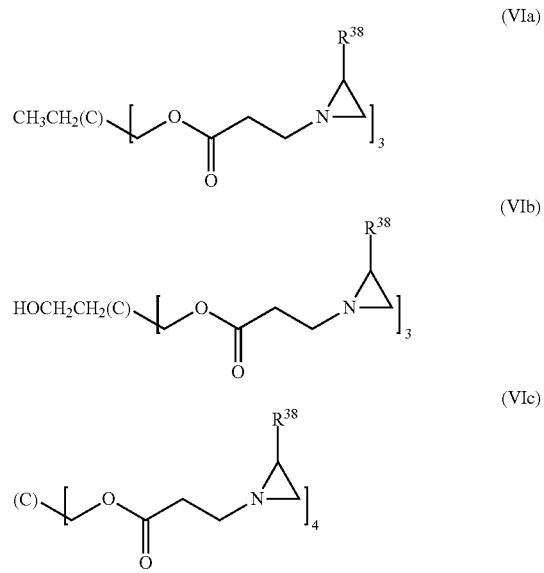

in which
$R^{38}$ is hydrogen or $CH_3$.

A particularly preferred product is the aziridine compound of the formula (VIa), with $R^{38}$=methyl, also known as Crosslinker CX-100 from DSM, and the hardener product "Corial Härter AN" from BASF, which comprises the aziridine of the formula (VIa) with $R^{38}$=hydrogen.

In one embodiment the nitrogen containing polymers are obtained by reaction of aziridines, such as more particularly those specified above, in the presence of water and optionally in the presence of cosolvents.

The invention accordingly also encompasses a method for producing nitrogen containing polymers that is characterized in that aziridines are reacted in the presence of water and optionally cosolvents.

The amount of water used here may be varied within a wide range. Generally speaking at least 10% by weight of water is used, based on the aziridines employed. The water amount is preferably 20% to 1000% by weight, more preferably 30% to 300% by weight, based on the aziridines employed. There is in principle no upper limit on the amount of water that can be used, although high water amounts naturally make it more costly and inconvenient to isolate the nitrogen containing polymers.

The reaction temperature is for example 30 to 100° C., preferably 40 to 90° C. and very preferably 50 to 80° C.

The reaction is preferably conducted until 95% or more, preferably 98% or more, more preferably 99% or more of the aziridine employed has been reacted, based on the fraction of aziridine rings. With very particular preference the reaction is conducted until aziridine rings are no longer detectable.

Accordingly, the nitrogen containing polymers employed in accordance with the invention have a fraction of 5% or less, preferably 2% or less, more preferably 1% or less, and very preferably no detectable amounts of aziridine rings, based on the aziridines employed.

In another embodiment the nitrogen containing polymers employed in accordance with the invention have a fraction of 5% or less, preferably 2% or less, more preferably 1% or less, and very preferably no detectable amounts of aziridine nitrogen, based on the total nitrogen content.

The fraction of unreacted aziridine rings can be determined by means, for example, of 13C NMR spectra in comparison to the aziridine employed.

The reaction time is generally 2 to 48 h, very preferably 3 to 24 h.

While the use of cosolvents is not absolutely necessary for achieving the desired stabilization, it may nevertheless be useful, particularly when employing high concentrations of aziridine, since it allows gelling within the reaction batch to be effectively prevented.

Cosolvents which can be used are in general all compounds which are miscible with water and which under the reaction conditions do not themselves react, or else react only to a minor extent, with the aziridines employed.

Preferred cosolvents are oligo- or polyalkylene glycols or triols, or ethers of the aforementioned compounds, having more particularly a molecular weight of less than 1000 g/mol. Particularly preferred are ethylene glycol, diethylene glycol, triethylene glycol, tetraethylene glycol, polyethylene glycol, propylene glycol, dipropylene glycol, polypropylene glycol, glycerol and also mono-, di-methyl, -ethyl, -propyl or -butyl ethers of the aforementioned compounds, and also any desired mixtures of the aforementioned cosolvents.

Especially preferred for use as cosolvent is diethylene glycol butyl ether.

The amount of cosolvents used can be varied within a wide range. Generally speaking, for example, at least 20% by weight of cosolvents are used, based on the amount of water employed, preferably 30% to 1000% by weight, more preferably 50% to 300% by weight.

The nitrogen containing polymers produced by the method of the invention can be used directly in the form of the resulting solution to stabilize iodine containing compounds, or optionally in isolated form following removal of cosolvents and/or water.

On the basis of their stabilizing action, the nitrogen containing polymers such as, more particularly, the nitrogen containing polymers obtainable in accordance with the invention and/or produced by the method of the invention are suitable for joint application with iodine containing compounds in biocidal compositions.

The invention therefore also embraces biocidal compositions comprising at least
a) at least one iodine containing compound having a biocidal action
b) at least one nitrogen containing polymer,
the individual components being subject to the abovementioned ranges and preference ranges in the same way.

Preferred biocidal compositions comprise
  a) IPBC and
  b) nitrogen containing polymers obtainable by reaction of at least one, preferably precisely one, aziridine of the formula (VI) in the presence of water.

The biocidal compositions of the invention comprise in general
a) 0.01% to 70% by weight, preferably 0.05% to 60% by weight, more preferably 0.1% to 50% by weight of iodine containing compounds having a biocidal action and
b) 0.001% to 50% by weight, preferably 0.005 to 40% by weight, more preferably 0.01% to 30% by weight of nitrogen containing polymers.

The biocidal compositions of the invention preferably comprise the iodine containing compounds with a biocidal action and the nitrogen containing polymers in a sum total of 0.011% to 100% by weight, preferably 0.05% to 80% by weight, more preferably 0.1% to 60% by weight.

In one embodiment the biocidal compositions of the invention comprise from 1% to 280% by weight of nitrogen containing polymers, preferably 2% to 225% by weight, more particularly 5% to 110% by weight, based on the iodine containing compounds having a biocidal action.

The biocidal compositions may further comprise solvents, or not.

The solvents optionally present may if used be solvents of the kind already described above as cosolvents for the reaction to give nitrogen containing polymers. The ranges and preference ranges apply here analogously.

The biocidal compositions may further comprise acids, such as organic and/or inorganic acids, for example, or not.

To the skilled person it is clear that in view of the possible basicity of the nitrogen containing polymers, especially if obtained from aziridines, the acids are present at least not completely in free form in the biocidal composition. The quantity figures given below therefore relate to levels and amounts in each case calculated on the basis of the free acid.

The inorganic acids optionally present may in principle be any inorganic acids that are soluble in the biocidal composition. Preferred inorganic acids are hydrochloric acid or HCl, sulphuric acid and phosphoric acid.

The organic acids optionally present may in principle be any organic acids which are soluble in the biocidal composition. Preferred organic acids are formic acid, acetic acid, citric acid, propionic acid or benzoic acid. Formic acid is particularly preferred.

The level of acids may be varied within a wide range. In general it is 0.01% to 2% by weight, preferably 0.03% to 1.5% by weight and very preferably 0.05% to 1% by weight, based on the overall biocidal composition.

The above-described biocidal compositions may additionally comprise other active ingredients and auxiliaries as well. They may take the form, for example, of a solution, emulsion or suspension.

It is possible for example for organic solvents to be included, or not.

Examples of organic solvents contemplated include aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, e.g. petroleum fractions (white spirit, Shellsol D60 from Shell Chemical), monohydric alcohols such as, for example, ethanol, isopropanol and butanol, polyhydric alcohols such as, for example, glycerol, pentaerythritol, polyvinyl alcohol (e.g. Mowiol® from Kuraray), glycols such as, for example, ethylene glycol and propylene glycol, oligoglycols and polyglycols, ethers of oligoglycols such as, for example, dipropylene glycol monomethyl ether (e.g. Dowanol® TPM from Dow), ethers and esters of alcohols such as (Texanol® from Eastman), ketones, such as acetone, methyl ethyl ketone, methyl isobutyl ketone or cyclohexanone, strongly polar aprotic solvents, such as dimethylformamide and dimethyl sulphoxide, and also, for example, totally etherified glycols, oligoglycols and polyglycols such as, for example, ethylene glycol dibutyl ether, etherified polyols and esterified polyols, esters of monobasic and polybasic carboxylic acids, e.g. diisobutyl adipate, diisobutyl maleate (e.g. Rhodiasolv DIB®).

Further possible ingredients of the biocidal compositions of the invention that may be included or not are adhesives such as carboxymethylcellulose, natural and synthetic polymers in powder, particle or latex form, such as gum arabic, polyvinyl alcohol, polyvinyl acetate, and also natural phospholipids, such as cephalins and lecithins, and synthetic phospholipids, and also mineral and vegetable oils.

Moreover, the biocidal compositions of the invention may comprise as further ingredients colourants such as inorganic pigments, e.g. iron oxide, titanium oxide, Prussian Blue, and organic dyes, such as alizarin dyes, azo dyes and metal phthalocyanine dyes.

Furthermore, the biocidal compositions of the invention may also comprise further stabilizers, such as, for example, chelating reagents or organic epoxides. In many cases here synergistic effects are observed.

The activity and the spectrum of action of the biocidal compositions of the invention may be increased if they include optionally further active ingredients selected from the group of further antimicrobially active compounds, fungicides, bactericides, herbicides, insecticides or other active ingredients.

In many cases, synergistic effects are obtained, i.e. the activity of the mixture is greater than the activity of the individual components. The following compounds, for example, are particularly favourable co-components, and may each individually be included or not:

triazoles such as: azaconazole, azocyclotin, bitertanol, bromuconazole, cyproconazole, diclobutrazole, difenoconazole, diniconazole, epoxiconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazol, penconazole, propiconazole, prothioconazole, simeconazole, (±)-cis-1-(4-chlorophenyl)-2-(1H-1,2,4-triazol-1-yl)cycloheptanol, 2-(1-tert-butyl)-1-(2-chlorophenyl)-3-(1,2,4-triazol-1-yl)propan-2-ol, tebuconazole, tetraconazole, triadimefon, triadimenol, triapenthenol, triflumizole, triticonazole, uniconazole and their metal salts and acid adducts;

imidazoles such as:
clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chloro-phenoxy)-3,3-dimethylbutan-2-one, and their metal salts and acid adducts;

pyridines and pyrimidines such as:
ancymidol, buthiobate, fenarimol, mepanipyrin, nuarimol, pyroxyfur, triamirol;

succinate dehydrogenase inhibitors such as:
benodanil, carboxim, carboxim sulphoxide, cyclafluramid, fenfuram, flutanil, furcarbanil, furmnecyclox, mebenil, mepronil, methfuroxam, metsulfovax, nicobifen, pyracarbolid, oxycarboxin, Shirlan, Seedvax;

naphthalene derivatives such as:
terbinafine, naftifine, butenafine, 3-chloro-7-(2-aza-2,7,7-trimethyloct-3-en-5-yne);

sulphenamides such as:
dichlofluanid, tolylfluanid, folpet, fluorofolpet, captan, captofol;

benzimidazoles such as:
carbendazim, benomyl, fuberidazole, thiabendazole or their salts;

morpholine derivatives such as:
aldimorph, dimethomorph, dodemorph, falimorph, fenpropidin, fenpropimorph, tridemorph, trimorphamid and their arylsulphonate salts such as, for example, p-toluenesulphonic acid and p-dodecylphenylsulphonic acid;

benzothiazoles such as:
2-mercaptobenzothiazole;

benzothiophene dioxides such as:
N-cyclohexyl-benzo[b]thiophenecarboxamide S,S-dioxide;

benzamides such as:
2,6-dichloro-N-(4-trifluoromethylbenzyl)benzamide, tecloftalam;

boron compounds such as:
boric acid, boric esters, borax;

formaldehyde and formaldehyde-releasing compounds such as:
benzyl alcohol mono(poly)hemiformal, 1,3-bis(hydroxymethyl)-5,5-dimethylimidazolidine-2,4-dione (DMDMH), bisoxazolidine, n-butanol hemiformal, cis-1-(3-chloroallyl)-3,5,7-triaza-1-azoniaadamantane chloride, 1-[1,3-bis(hydroxymethyl-2,5-dioxoimidazolidin-4-yl]-1,3-bis-(hydroxymethyl)urea, dazomet, dimethylolurea, 4,4-dimethyloxazolidine, ethylene glycol hemiformal, 7-ethylbicyclooxazolidine, hexahydro-S-triazine, hexamethylenetetramine, N-hydroxymethyl-N'-methylthiourea, methylenebismorpholine, sodium N-(hydroxymethyl)glycinate, N-methylolchloroacetamide, oxazolidine, paraformaldehyde, taurolin, tetrahydro-1,3-oxazine, N-(2-hydroxypropyl) aminemethanol, tetramethylolacetylenediurea (TMAD);

isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone, N-octylisothiazolin-3-one, 4,5-trimethyleneisothiazolinone, 4,5-benzisothiazolinone;

aldehydes such as:
cinnamaldehyde, formaldehyde, glutaraldehyde, β-bromocinnamaldehyde, o-phthalaldehyde;

thiocyanates such as:
thiocyanatomethylthiobenzothiazole, methylenebisthiocyanate;

quaternary ammonium compounds and guanidines such as:
benzalkonium chloride, benzyldimethyltetradecylammonium chloride, benzyldimethyl-dodecylammonium chloride, dichlorobenzyldimethylalkylammonium chloride, didecyldimethyl-ammonium chloride, dioctyldimethylammonium chloride, N-hexadecyltrimethylammonium chloride, 1-hexadecylpyridinium chloride, iminoctadine tris(albesilate);

phenols such as:
tribromophenol, tetrachlorophenol, 3-methyl-4-chlorophenol, 3,5-dimethyl-4-chlorophenol, dichlorophene, 2-benzyl-4-chlorophenol, triclosan, diclosan, hexachlorophene, methyl p-hydroxybenzoate, ethyl p-hydroxybenzoate, propyl p-hydroxybenzoate, butyl p-hydroxybenzoate, octyl p-hydroxybenzoate, o-phenylphenol, m-phenylphenol, p-phenylphenol, 4-(2-tert-butyl-4-methylphenoxy)phenol, 4-(2-isopropyl-4-methylphenoxy)phenol, 4-(2,4-dimethylphenoxy)phenol and their alkali metal salts and alkaline earth metal salts;

microbicides with an activated halogen group such as:
bronopol, bronidox, 2-bromo-2-nitro-1,3-propanediol, 2-bromo-4'-hydroxyacetophenone, 1-bromo-3-chloro-4,4,5,5-tetramethyl-2-imidazolidinone, β-bromo-β-nitrostyrene, chloroacetamide, chloramine T, 1,3-dibromo-4,4,5,5-tetramethyl-2-imidazolidinone, dichloroamine T, 3,4-dichloro-(3H)-1,2-dithiol-3-one, 2,2-dibromo-3-nitrilipropionamide, 1,2-dibromo-2,4-dicyanobutane, halane, halazone, mucochloric acid, phenyl 2-chlorocyanovinyl sulphone, phenyl 1,2-dichloro-2-cyanovinyl sulphone, trichloroisocyanuric acid;

pyridines such as:
1-hydroxy-2-pyridinethione (and the Cu, Na, Fe, Mn, Zn salts thereof), tetrachloro-4-methyl-sulphonylpyridine, pyrimethanol, mepanipyrim, dipyrithion, 1-hydroxy-4-methyl-6-(2,4,4-trimethyl-pentyl)-2(1H)-pyridine;

methoxyacrylates or similar such as:
azoxystrobin, dimoxystrobin, fluoxastrobin, kresoxim-methyl, metominostrobin, orysastrobin, picoxystrobin, pyraclostrobin, trifloxystrobin, 2,4-dihydro-5-methoxy-2-methyl-4-[2-[[[[1-[3-(trifluoromethyl)phenyl]ethylidene]amino]oxy]methyl]phenyl]-3H-1,2,4-triazol-3-one (CAS No. 185336-79-2);

metal soaps such as:

salts of the metals tin, copper and zinc with higher fatty acids, resin acids, naphthenic acids and phosphoric acid, such as, for example, tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;

metal salts such as:

salts of the metals tin, copper, zinc, and also chromates and dichromates, such as, for example, copper hydroxycarbonate, sodium dichromate, potassium dichromate, potassium chromate, copper sulphate, copper chloride, copper borate, zinc fluorosilicate, copper fluorosilicate;

oxides such as:

oxides of the metals tin, copper and zinc, such as, for example, tributyltin oxide, $Cu_2O$, CuO, ZnO;

oxidizing agents such as:

hydrogen peroxide, peracetic acid, potassium persulphate;

dithiocarbamates such as:

cufraneb, ferban, potassium N-hydroxymethyl-N'-methyldithiocarbamate, sodium dimethyldithiocarbamate, potassium dimethyldithiocarbamate, mancozeb, maneb, metam, metiram, thiram, zineb, ziram;

nitriles such as:

2,4,5,6-tetrachloroisophthalonitrile, disodium cyanodithioimidocarbamate;

quinolines such as:

8-hydroxyquinoline and the copper salts thereof;

other fungicides and bactericides such as:

bethoxazin, 5-hydroxy-2(5H)-furanone, 4,5-benzodithiazolinone, 4,5-trimethylenedithiazolinone, N-(2-p-chlorobenzoylethyl)hexaminium chloride, 2-oxo-2-(4-hydroxyphenyl)acetohydroxycinnamoyl chloride, tris-N-(cyclohexyldiazeniumdioxy)-aluminium, N-(cyclohexyldiazeniumdioxy)-tributyltin or its potassium salts, bis-N-(cyclohexyldiazeniumdioxy) copper, iprovalicarb, fenhexamide, spiroxamine, carpropamid, diflumetorin, quinoxyfen, famoxadone, polyoxorim, acibenzolar S-methyl, furametpyr, thifluzamide, methalaxyl-M, benthiavalicarb, metrafenon, cyflufenamid, tiadinil, tea tree oil, phenoxyethanol, Ag, Zn or Cu-containing zeolites alone or incorporated into polymeric materials.

Very especially preferred are mixtures with azaconazole, bromuconazole, cyproconazole, dichlobutrazol, diniconazole, diuron, hexaconazole, metaconazole, penconazole, propiconazole, tebuconazole, dichlofluanid, tolylfluanid, fluorfolpet, methfuroxam, carboxin, N-cyclohexyl-benzo[b]thiophenecarboxamide S,S-dioxide, fenpiclonil, 4-(2,2-difluoro-1,3-benzodioxol-4-yl)-1H-pyrrole-3-carbonitrile, butenafine, imazalil, N-methylisothiazolin-3-one, 5-chloro-N-methylisothiazolin-3-one, N-octylisothiazolin-3-one, dichloro-N-octylisothiazolinone, mercaptobenzothiazole, thiocyanatomethylthiobenzothiazole, thiabendazole, benzoisothiazolinone, N-(2-hydroxypropyl)aminomethanol, benzyl alcohol (hemi)formal, N-methylolchloroacetamide, N-(2-hydroxypropyl)aminemethanol, glutaraldehyde, omadine, Zn-omadine, dimethyl dicarbonate, 2-bromo-2-nitro-1,3-propanediol, bethoxazin, o-phthalialdehyde, 2,2-dibromo-3-nitrilipropionamide, 1,2-dibromo-2,4-dicyanobutane, 1,3-bis(hydroxymethyl)-5,5-dimethylimidazolidine-2,4-dione (DMDMH), tetramethylolacetylenediurea (TMAD), ethylene glycol hemiformal, p-hydroxybenzoic acid, carbendazim, chlorphen, 3-methyl-4-chlorophenol, o-phenylphenol.

Apart from with the abovementioned fungicides and bactericides, mixtures with a good efficacy are, moreover, also prepared with other active ingredients:

insecticides/acaricides/nematicides:

abamectin, acephate, acetamiprid, acetoprole, acrinathrin, alanycarb, aldicarb, aldoxycarb, aldrin, allethrin, alpha-cypermethrin, amidoflumet, amitraz, avermectin, azadirachtin, azinphos A, azinphos M, azocyclotin,

*Bacillus thuringiensis*, barthrin, 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bistrilfluron, bromophos A, bromophos M, bufencarb, buprofezin, butathiophos, butocarboxim, butoxycarboxim, cadusafos, carbaryl, carbofuran, carbophenothion, carbosulfan, cartap, quinomethionate, cloethocarb, chlordane, chlorethoxyfos, chlorfanapyr, chlorfenvinphos, chlorfluazuron, chlormephos, N-[(6-chloro-3-pyridinyl)methyl]-N'-cyano-N-methylethanimidamide, chlorpicrin, chlorpyrifos A, chlorpyrifos M, cis-resmethrin, clocythrin, clothiazoben, cypophenothrin, clofentezine, coumaphos, cyanophos, cycloprothrin, cyfluthrin, cyhalothrin, cyhexatin, cypermethrin, cyromazin, decamethrin, deltamethrin, demeton M, demeton S, demeton-S-methyl, diafenthiuron, dialiphos, diazinon, 1,2-dibenzoyl-1(1,1-dimethyl)hydrazine, DNOC, dichlofenthion, dichlorvos, dicliphos, dicrotophos, difethialone, diflubenzuron, dimethoate, 3,5-dimethylphenyl methylcarbamate, dimethyl(phenyl)silylmethyl-3-phenoxybenzyl ether, dimethyl(4-ethoxyphenyl)silylmethyl-3-phenoxybenzyl ether, dimethylvinphos, dioxathion, disulfoton, eflusilanate, emamectin, empenthrin, endosulfan, EPN, esfenvalerate, ethiofencarb, ethion, ethofenprox, etrimphos, etoxazole, etobenzanid, fenamiphos, fenazaquin, fenbutatin oxide, fenfluthrin, fenitrothion, fenobucarb, fenothiocarb, fenoxycarb, fenpropathrin, fenpyrad, fenpyroximate, fensulfothion, fenthion, fenvalerate, fipronil, flonicamid, fluacrypyrim, fluazuron, flucycloxuron, flucythrinate, flufenerim, flufenoxuron, flupyrazofos, flufenzine, flumethrin, flufenprox, fluvalinate, fonophos, formethanate, formothion, fosmethilan, fosthiazate, fubfenprox, furathiocarb, halofenozide, HCH (CAS RN: 58-89-9), heptenophos, hexaflumuron, hexythiazox, hydramethylnon, hydroprene, imidacloprid, imiprothrin, indoxycarb, iprinomectin, iprobenfos, isazophos, isoamidophos, isofenphos, isoprocarb, isoprothiolane, isoxathion, ivermectin, kadedrin, lambda-cyhalothrin, lufenuron, malathion, mecarbam, maervinphos, mesulfenphos, metaldehyde, methacrifos, methamidophos, methidathion, methiocarb, methomyl, metolcarb, milbemectin, monocrotophos, moxiectin, naled, NI 125, nicotine, nitenpyram, noviflumuron, ometohate, oxamyl, oxydemethon M, oxydeprofos, parathion A, parathion M, penfluron, permethrin, 2-(4-phenoxyphenoxy)ethyl ethylcarbamate, phenthoate, phorate, phosalon, phosmet, phosphamidon, phoxim, pirimicarb, pirimiphos M, pirimiphos A, prallethrin, profenophos, promecarb, propaphos, propoxur, prothiophos, prothoate, pymetrozin, pyrachlophos, pyridaphenthion, pyresmethrin, pyrethrum, pyridaben, pyridalyl, pyrimidifen, pyriproxifen, pyrithiobac-sodium, quinalphos,
resmethrin, rotenone,
salithion, sebufos, silafluofen, spinosad, spirodiclofen, spiromesifen, sulfotep, sulprofos,
tau-fluvalinate, tar oils, tebufenozide, tebufenpyrad, tebupirimphos, teflubenzuron, tefluthrin, temephos, terbam, terbufos, tetrachlorvinphos, taramethrin, terametharcarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamate, triazuron, trichlorfon, triflumuron, trimethacarb,
vamidothion, xylylcarb, zetamethrin;
molluscicides:
fentin acetate, metaldehyde, methiocarb, niclosamide;
herbicides and algicides:
acetochlor, acifluorfen, aclonifen, acrolein, alachlor, alloxydim, ametryn, amidosulfuron, amitrole, ammonium sulfamate, anilofos, asulam, atrazine, azafenidin, aziprotryne, azimsulfuron,
benazolin, benfluralin, benfuresate, bensulfuron, bensulfide, bentazone, benzofencap, benzthiazuron, bifenox, bispyribac, bispyribac-sodium, borax, bromacil, bromobutide, bromofenoxim, bromoxynil, butachlor, butamifos, butralin, butylate, bialaphos, benzoyl-prop, bromobutide, butroxydim, carbetamide, carfentrazone-ethyl, carfenstrole, chlomethoxyfen, chloramben, chlorbromuron, chloroflurenol, chloridazon, chlorimuron, chlornitrofen, chloroacetic acid, chloransulam-methyl, cinidon-ethyl, chlorotoluron, chloroxuron, chlorpropham, chlorsulfuron, chlorthal, chlorthiamid, cinmethylin, cinosulfuron, clefoxydim, clethodim, clomazone, chlomeprop, clopyralid, cyanamide, cyanazine, cycloate, cycloxydim, chloroxynil, clodinafop-propargyl, cumyluron, clometoxyfen, cyhalofop, cyhalofop-butyl, clopyrasulfuron, cyclosulfamuron,
diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D,
daimuron, dalapon, dazomet, 2,4-DB, desmedipham, desmetryn, dicamba, dichlobenil, dimethamid, dithiopyr, dimethametryn,
eglinazine, endothal, EPTC, esprocarb, ethalfluralin, ethidimuron, ethofumesate, ethobenzanid, ethoxyfen, ethametsulfuron, ethoxysulfuron,
fenoxaprop, fenoxaprop-P, fenuron, flamprop, flamprop-M, flazasulfuron, fluazifop, fluazifop-P, fuenachlor, fluchloralin, flufenacet, flumeturon, fluorocglycofen, fluoronitrofen, flupropanate, flurenol, fluridone, fluorochloridone, fluroxypyr, fomesafen, fosamine, fosametine, flamprop-isopropyl, flamprop-isopropyl-L, flufenpyr, flumiclorac-pentyl, flumipropyn, flumioxzim, flurtamone, flumioxzim, flupyrsulfuron-methyl, fluthiacet-methyl,
glyphosate, glufosinate-ammonium
haloxyfop, hexazinone,
imazamethabenz, isoproturon, isoxaben, isoxapyrifop, imazapyr, imazaquin, imazethapyr, ioxynil, isopropalin, imazosulfuron, imazomox, isoxaflutole, imazapic,
ketospiradox,
lactofen, lenacil, linuron,
MCPA, MCPA-hydrazide, MCPA-thioethyl, MCPB, mecoprop, mecoprop-P, mefenacet, mefluidide, mesosulfuron, metam, metamifop, metamitron, metazachlor, methabenzthiazuron, methazole, methoroptryne, methyldymron, methyl isothiocyanate, metobromuron, metoxuron, metribuzin, metsulfuron, molinate, manolide, monolinuron, MSMA, metolachlor, metosulam, metobenzuron,
naproanilide, napropamide, naptalam, neburon, nicosulfuron, norflurazon, sodium chlorate,
oxadiazon, oxyfluorfen, oxysulfuron, orbencarb, oryzalin, oxadiargyl,
propyzamide, prosulfocarb, pyrazolate, pyrazosulfuron, pyrazoxyfen, pyribenzoxim, pyributicarb, pyridate, paraquat, pebulate, pendimethalin, pentachlorophenol, pentoxazone, pentanochlor, petroleum oils, phenmedipham, picloram, piperophos, pretilachlor, primisulfuron, prodiamine, profoxydim, prometryn, propachlor, propanil, propaquizafob, propazine, propham, propisochlor, pyriminobac-methyl, pelargonic acid, pyrithiobac, pyraflufen-ethyl,
quinmerac, quinocloamine, quizalofop, quizalofop-P, quinchlorac,
rimsulfuron,
sethoxydim, sifuron, simazine, simetryn, sulfosulfuron, sulfometuron, sulfentrazone, sulcotrione, sulfosate,
tar oils, TCA, TCA-sodium, tebutam, tebuthiuron, terbacil, terbumeton, terbuthylazine, terbutryn, thiazafluoron, thifensulfuron, thiobencarb, thiocarbazil, tralkoxydim, triallate, triasulfuron, tribenuron, triclopyr, tridiphane, trietazine, trifluoralin, tycor, thdiazimin, thiazopyr, triflusulfuron,
vernolate.

The biocidal compositions are especially suitable for imparting biocidal properties to industrial materials such as, more particularly, coating materials such as, for example, paints, varnishes, primers, impregnating systems and stains.

Particularly in binder formulations comprising alkyd resin, especially if they include transition metal dryers and/or transition metal compounds as pigments, is the stabilizing effect of the nitrogen containing polymers on the iodine containing compounds with a biocidal action manifested in a particularly advantageous way.

The invention therefore further provides binder formulations comprising
a) at least one binder,
b) at least one iodine containing compound having a biocidal action and
c) at least one nitrogen containing polymer
the individual components being subject in the same way to abovementioned ranges and preference ranges.

Preferred binders are oxidatively drying binders, such as, for example, alkyd resin containing binders, or binders which film by means of coalescents, such as polymer latices in particular.

The alkyd resins are, in general, polycondensation resins formed from polyols and polybasic carboxylic acids and/or their anhydrides, and fats, oils or free natural and/or synthetic fatty acids. The alkyd resins may optionally also be modified chemically with hydrophilic groups, especially water-soluble groups, in order that they can be used, for example, as an emulsifiable or as a water-soluble alkyd resin.

The stated polyols are preferably glycerol, pentaerythritol, trimethylolethane, trimethylolpropane and various diols such as ethane-/propanediol, diethylene glycol and neopentyl glycol.

The stated polybasic carboxylic acids and/or their anhydrides are preferably phthalic acid, phthalic anhydride, maleic anhydride, isophthalic acid, terephthalic acid, trimellitic anhydride, adipic acid, azelaic acid or sebacic acid.

The stated oils or fatty acids are generally linseed oil, oiticica oil, tung oil, soya oil, sunflower oil, safflower oil, ricinene oil, tall oil, castor oil, coconut oil, peanut oil, their fatty acids, and also synthetic monocarboxylic acids.

The alkyd resins can optionally also be modified with, for example, natural resins, phenolic resins, acrylic resins, styrene, epoxy resins, silicone resins, isocyanates, polyamides or aluminium alkoxides.

The alkyd resins generally have a molar mass of 500 to 100 000 g/mol, preferably of 1000 to 50000 g/mol, more particularly of 1500 to 20000 g/mol, determined preferably by laser light scattering; see, for example, "Static Light Scattering of Polystyrene Reference Materials: Round Robin Test", UJust, B. Werthmann International Journal of Polymer Analysis and Characterization, 1999 Vol. 5, pages 195-207.

The binder formulations of the invention comprise preferably 1% to 80%, more preferably 2% to 70% and with particular preference 3% to 60% by weight of binder, preferably alkyd resin.

The binder formulation of the invention preferably further comprises at least one transition metal dryer. Transition metal dryers for the purposes of this specification are more particularly transition metal compounds which enable or accelerate the drying and curing of alkyd containing resin-based binders.

Preference is given to the salts of transition metals of groups Vb, VIb, VIIb, VIII and Ib of the chemical periodic system. These are more particularly the salts of cobalt, manganese, vanadium, nickel, copper and iron, more preferably cobalt, manganese, iron and vanadium. They need not necessarily be used alone, but instead can also be employed in combination with non-transition metal salts, such as lead, calcium or zirconium, for example.

The preferred transition metal salts are soluble in white spirit at 20° C. in an amount of more than 10 g/l. The salts in question are preferably the salts of carboxylic acids, which have high compatibility with the alkyd resins and at the same time ensure sufficient solubility of the metal salt Preference is given to using transition metal salts of fatty acids such as oleates or linoleates, resin acids such as resinates, or salts of 2-ethylhexanoic acid (octoates). Preferred transition metal dryers are cobalt octoate and cobalt naphthenate, e.g. Octa-soligen®-Cobalt 12 from Borchers.

The binder formulations of the invention preferably comprise the transition metal dryers in an amount of 0.001% to 1%, preferably 0.005% to 0.5% and very preferably 0.01% to 0.1% by weight, based in each case on the binder, preferably alkyd resin.

In one preferred embodiment the binder formulations comprise at least one polar organic solvent, preferably a polar protic organic solvent. Examples of suitable polar protic organic solvents include are those such as dipropylene glycol monomethyl ether (e.g. Dowanol DPM from Dow Chemical) and also, alternatively, preferably in addition thereto, polar aprotic organic solvents, such as dimethylformamide and dimethyl sulphoxide, and also, for example, etherified glycols, oligoglycols and polyglycols, etherified polyols and esterified polyols, esters of monobasic and polybasic carboxylic acids, e.g. diisobutyl adipate, diisobutyl maleate (e.g. Rhodiasolv DIB).

Particular preference is given to a binder formulation comprising
1% to 80%, preferably 2% to 70%, more preferably 3% to 60% by weight of alkyd resin
0% to 50%, preferably 0% to 45%, more preferably 0% to 40% by weight of pigments
0.01% to 5%, preferably 0.05% to 3%, more preferably 0.1% to 2% by weight of iodine containing compounds with a biocidal action, preferably IBPC
0.001% to 5%, preferably 0.005% to 3%, more preferably 0.01% to 2% by weight of nitrogen containing polymer
2% to 97% by weight of solvent(s), preferably those as described above for the biocidal compositions and 0.001% to 3% by weight of a transition metal dryer.

The binder formulation may further comprise or not comprise the following, in each case independently of one another: fillers, anti-skinning agents, rheological additives such as, for example, anti-settling agents and thixotropic agents, further antimicrobially active compounds, fungicides, bactericides, herbicides, insecticides or other active ingredients; for the antimicrobially active compounds, fungicides, bactericides, herbicides, insecticides or other active ingredients, the statements made above in respect of the biocidal compositions apply equally here.

The binder formulation may further comprise or not comprise the following, in each case independently of one another: solvents, process additives, plasticizers, heat stabilizers, and corrosion inhibitors.

Furthermore, the biocidal compositions or binder formulations of the invention may also further comprise one or more auxiliaries from the series of the antioxidants, radical scavengers, UV stabilizers, chelating agents and UV absorbers. In some such cases synergistic effects are observed.

UV stabilizers that may be mentioned include, by way of example, the following:
sterically hindered phenols, such as
2,6-di-tert-butyl-4-methylphenol, 2-tert-butyl-4,6-dimethylphenol, 2,6-di-cyclopentyl-4-methylphenol, 2-(α-methylcyclohexyl)-4,6-dimethylphenol, 2,6-di-octadecyl-4-methylphenol or 2,6-di-tert-butyl-4-methoxymethylphenol, diethyl(3,5-di-ter-butyl-4-hydroxybenzyl)phosphonate, 2,4-dimethyl-6-(1-methylpentadecyl)phenol, 2-methyl-4,6-bis[(octylthio)methyl]phenol, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 2,2'-methylenebis(6-tert-butyl-4-methylphenol), 2,2'-methylenebis(4-methyl-6-cyclohexyl-phenol), 2,2'-methylenebis(4,6-di-tert-butylphenol), 2,2'-ethylidenebis(4,6-di-tert-butylphenol), 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 1,1,3-tris(5-tert-butyl-4-hydroxy-2-methyl-phenyl)butane, 1,3,5-tri(3,5-di-tert-butyl-4-hydroxybenzyl)-2,4,6-trimethylbenzene, isooctyl 3,5-di-tert-butyl-4-hydroxybenzylmercaptoacetate, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 1,3,5-tris[(3,5-di-tert-butyl-4-hydroxyphenyl) propionyloxyethyl]isocyanurate, dioctadecyl 3,5-di-tert-butyl-4-hydroxybenzylphosphonate, calcium monoethyl 3,5-di-tert-butyl-4-hydroxybenzylphosphonate, N,N-di-(3,5-di-tert-butyl-4-hydroxyphenylpropionyl) hexamethylenediamine, N,N'-di-(3,5-di-tert-butyl-4-hydroxyphenylpropionyl)trimethylenediamine, N,N'-di-(3,5-di-tert-butyl-4-hydroxyphenylpropionyl)hydrazine, 3,9-bis[1,1-dimethyl-2-[(3-tert-butyl-4-hydroxy-5-methylphenyl)propionyloxy]ethyl]-2,4,8,10-tetraoxaspiro [5.5]undecane, bis[3,3-bis(4'-hydroxy-3'-tert-butylphenyl) butanoic acid]ethylene glycol ester, 2,6-bis[[3-(1,1-dimethylethyl)-2-hydroxy-5-methylphenyl]octahydro-4,7-methano-1H-indenyl]-4-methylphenol (=Wingstay L), 2,4-bis(n-octylthio)-6-(3,5-di-tert-butyl-4-hydroxyphenylamino)-s-triazane, N-(4-hydroxy-phenyl) octadecanamide, 2,4-di-tert-butylphenyl 3',5'-di-tert-butyl-4-hydroxybenzoate, (benzoic acid, 3,5-bis(1,1-dimethylethyl)-4-hydroxy-, hexadecyl ester), 3-hydroxyphenyl benzoate, 2,2'-methylenebis(6-tert-butyl-4-methylphenol)monoacrylate, 2-(1,1-dimethylethyl)-6-[1-[3-(1,1-dimethylethyl)-5-(1,1-dimethylpropyl)-2-hydroxyphenyl]ethyl]-4-(1,1-dimethylpropyl)phenyl ester, esters of β-(3,5-di-tert-butyl-4-hydroxyphenyl)propionic acid with monohydric or polyhydric alcohols such as, for example, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide, esters of β-(5-tert-butyl-4-hydroxy-3-methylphenyl)propionic acid with monohydric or polyhydric alcohols such as, for example, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide.

Hindered amines, such as
bis(1,2,2,6,6-pentamethyl-4-piperidyl) 2-(3,5-di-tert-butyl-4-hydroxybenzyl)-2-butylmalonate, bis(2,2,6,6-tetramethyl-4-piperidyl)decanedioate, dimethyl succinate-1-(2-hydroxyethyl)-4-hydroxy-2,2,6,6-tetramethylpiperidine copolymer, poly[[6-[(1,1,3,3-tetramethylbutyl)amino]-1,3,5-triazine-2,4-diyl][(2,2,6,6-tetramethyl-4-piperidyl)imino]hexamethylene[(2,2,6,6-tetramethyl-4-piperidyl)imino]](CAS No. 71878-19-8), 1,5,8,12-tetrakis[4,6-bis(n-butyl-n-1,2,2,6,6-pentamethyl-4-piperidylamino)-1,3,5-triazin-2-yl]-1,5,8,12-tetraazadodecane (CAS No. 106990-43-6), bis(1,2,2,6,6-pentamethyl-4-piperidyl)decanedioate, bis(1,2,2,6,6-pentamethyl-4-piperidyl) 2-(3,5-di-tert-butyl-4-hydroxybenzyl)-2-butylmalonate, decanedioic acid, bis(2,2,6,6-tetramethyl-4-piperidinyl) ester, reaction products with tert-butyl hydroperoxide and octane (CAS No. 129757-67-1), Chimasorb 2020 (CAS No. 192268-64-7), poly[[6-morpholino-1,3,5-triazine-2,4-diyl]][(2,2,6,6-tetramethyl-4-piperidinyl)imino]-1,6-hexanediyl[(2,2,6,6-tetramethyl-4-piperidinyl)imino]], poly[[6-(4-morpholinyl)-1,3,5-triazine-2,4-diyl]-[(1,2,2,6,6-pentamethyl-4-piperidinyl)imino]-1,6-hexanediyl[(1,2,2,6,6-pentamethyl-4-piperidinyl)-imino]] (9CI), 3-dodecyl-1-(2,2,6,6-tetramethyl-4-piperidyl)pyrrolidine-2,5-dione, 3-dodecyl-1-(1,2,2,6,6-pentamethylpiperidin-4-yl)pyrrolidine-2,5-dione, 4-octadecanoyloxy-2,2,6,6-tetramethylpiperidine, poly[[6-(cyclohexylamino)-1,3,5-triazine-2,4-diyl][(2,2,6,6-tetramethyl-4-piperidinyl)-imino]-1,6-hexanediyl[(2,2,6,6-tetramethyl-4-piperidinyl)imino]], 1H,4H,5H,8H-2,3a,4a,6,7a,8a-hexaazacyclopenta[def]fluorene-4,8-dione, hexahydro-2,6-bis(2,2,6,6-tetramethyl-4-piperidinyl)- (CAS No. 109423-00-9), N,N'-bis(formyl)-N,N'-bis(2,2,6,6-tetramethyl-4-piperidyl)-1,6-hexane-diamine, N-(tetramethyl-4-piperidinyl)maleimide-C20-24-α-olefin copolymer (CAS No. 199237-39-3), tetrakis(1,2,2,6,6-pentamethyl-4-piperidyl) 1,2,3,4-butanetetracarboxylate, tetrakis(2,2,6,6-tetramethyl-4-piperidyl) 1,2,3,4-butanetetracarboxylate, 1,2,2,6,6-pentamethyl-4-piperidinyl tridecyl 1,2,3,4-butanetetracarboxylate, (1,2,3,4-butanetetracarboxylic acid, 2,2,6,6-tetramethyl-4-piperidinyl tridecyl ester), (2,4,8,10-tetraoxaspiro[5.5]undecane-3,9-diethanol, β,β,β',β'-tetramethyl-, polymer with 1,2,3,4-butanetetracarboxylic acid) (CAS No. 115055-30-6), 2,2,4,4-tetramethyl-21-oxo-7-oxa-3,20-diazadispiro[5.1.11.2]heneicosane, (7-oxa-3,20-diazadispiro[5.1.11.2]heneicosane-20-propanoic acid, 2,2,4,4-tetramethyl-21-oxo-, tetradecyl ester), (7-oxa-3,20-diazadispiro[5.1.11.2]heneicosane-21-one, 2,2,4,4-tetramethyl-20-(oxiranylmethyl)-), (propanamide, N-(2,2,6,6-tetramethyl-4-piperidinyl)-3-[(2,2,6,6-tetramethyl-4-piperidinyl)amino]-), (1,3-propanediamine, N,N'''-1,2-ethanediylbis-, polymer with 2,4,6-trichloro-1,3,5-triazine, reaction products with N-butyl-2,2,6,-tetramethyl-4-piperidin-amine) (CAS No. 136504-96-6), 1,1'-ethylenebis(3,3,5,5-tetramethyl-2-piperazinone), (piperazinone, 1,1',1''-[1,3,5-triazine-2,4,6-triyltris[(cyclohexylimino)-2,1-ethanediyl]] tris[3,3,5,5-tetramethyl-), (7-oxa-3,20-diazadispiro[5.1.11.2]heneicosane-20-propanoic acid, 2,2,4,4-tetramethyl-21-oxo-, dodecyl ester), 1,1-bis(1,2,2,6,6-pentamethyl-4-piperidyloxycarbonyl)-2-(4-methoxyphenyl)ethene, (2-propenoic acid, 2-methyl-, methyl ester, polymer with 2,2,6,6-tetramethyl-4-piperidinyl 2-propenoate) (CAS No. 154636-12-1), (propanamide, 2-methyl-N-(2,2,6,6-tetramethyl-4-piperidinyl)-2-[(2,2,6,6-tetramethyl-4-piperidinyl)amino]-), (D-glucitol, 1,3:2,4-bis-O-(2,2,6,6-tetramethyl-4-piperidinylidene)-) (CAS No. 99473-08-2), N,N'-bis(2,2,6,6-tetramethyl-4-piperidinyl)isophthalamide, 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, 1-(4-tert-butyl-2-butenyl)-4-hydroxy-2,2,6,6-tetramethylpiperidine, 4-stearoyloxy-2,2,6,6-tetramethylpiperidine, 1-ethyl-4-salicyloyloxy-2,2,6,6-tetramethylpiperidine, 4-methacryloyloxy-1,2,2,6,6-pentamethylpiperidine, 1,2,2,6,6-pentamethylpiperidin-4-yl β-(3,5-ditert-butyl-4-hydroxyphenyl)propionate, 1-benzyl-2,2,6,6-tetramethyl-4-piperidinyl maleate, (di-2,2,6,6-tetramethylpiperidin-4-yl) adipate, (di-2,2,6,6-tetramethylpiperidin-4-yl) sebacate, (di-1,2,3,3,6-tetramethyl-2,6-diethylpiperidin-4-yl) sebacate, (di-1-allyl-2,2,6,6-tetramethylpiperidin-4-yl)phthalate, 1-propargyl-4-β-cyanoethyloxy-2,2,6,6-tetramethylpiperidine, 1-acetyl-2,2,6,6-tetramethylpiperidin-4-yl acetate, trimellitic acid tri(2,2,6,6-tetramethylpiperidin-4-yl) ester, 1-acryloyl-4-benzyloxy-2,2,6,6-tetramethylpiperidine, dibutyl-malonic acid di(1,2,2,6,6-pentamethylpiperidin-4-yl) ester, butyl(3,5-di-tert-butyl-4-hydroxybenzyl)malonic acid di(1,2,2,6,6-pentamethylpiperidin-4-yl) ester, dibenzylmalonic acid di(1,2,2,6,6-pentamethylpiperidin-4-yl) ester, dibenzylmalonic acid di(1,2,3,6-tetramethyl-2,6-diethylpiperidin-4-yl) ester, hexane-1',6'-bis-(4-carbamoyloxy-1-n-butyl-2,2,6,6-tetramethylpiperidine), toluene-2',4'-bis(4-carbamoyloxy-1-n-propyl-2,2,6,6-tetramethylpiperidine), dimethyl-bis(2,2,6,6-tetramethylpiperidine-4-oxy)silane, phenyl-tris(2,2,6,6-tetramethylpiperidine 4-oxy)silane, tris(1-propyl-2,2,6,6-tetramethylpiperidin-4-yl)phosphite, tris(1-propyl-2,2,6,6-tetramethylpiperidin-4-yl)phosphate, phenyl[bis(1,2,2,6,6-pentamethylpiperidin-4-yl)]phosphonate, di(1,2,2,6,6-pentamethylpiperidin-4-yl) sebacate, N,N'-bis(2,2,6,6-tetramethylpiperidin-4-yl)hexamethylene-1,6-diamine, N,N'-bis(2,2,6,6-tetramethylpiperidin-4-yl)-hexamethylene-1,6-diacetamide, 1-acetyl-4-(N-cyclohexylacetamido)-2,2,6,6-tetramethylpiperidine, 4-benzylamino-2,2,6,6-tetramethylpiperidine, N,N'-bis(2,2,6,6-tetramethylpiperidin-4-yl)-N,N'-dibutyladipamide, N,N'-bis(2,2,6,6-tetramethylpiperidin-4-yl)-N,N'-dicyclohexyl(2-hydroxy-propylene), N,N'-bis(2,2,6,6-tetramethylpiperidin-4-yl)-p-xylylenediamine, 4-(bis-2-hydroxy-ethyl)amino-1,2,2,6,6-pentamethylpiperidine, 4-(3-methyl-4-hydroxy-5-text-butyl-benz-amido)-2,2,6,6-tetramethylpiperidine, 4-methacrylamino-1,2,2,6,6-pentamethylpiperidine, 9-aza-8,8,10,10-tetramethyl-1,5-dioxaspiro[5.5]undecane, 9-aza-8,8,10,10-tetramethyl-3-ethyl-1,5-dioxaspiro[5.5]-undecane, 8-aza-2,7,7,8,9,9-hexamethyl-1,4-dioxaspiro[4.5]decane, 9-aza-3-hydroxymethyl-3-ethyl-8,8,9,10,10-pentamethyl-1-5-dioxaspiro[5.5]undecane, 9-aza-3-ethyl-3-acetoxymethyl-9-acetyl-8,8,10,10-tetramethyl-1,5-dioxaspiro[5.5]undecane, 2,2,6,6-tetramethylpiperidine-4-spiro-2'-(1,3'-dioxane)-5'-spiro-5''-(1''',3'''-dioxane)-2-spiro-4''(2''',2''',6''',6'''-tetramethylpiperidine)-3-benzyl-1,3,8-triaza-7,7,9,9-tetramethyl-spiro[4.5]decane-2,4-dione, 3-n- octyl-1,3,8-triaza-7,7,9,9-tetramethyl-spiro[4.5]decane-2,4-dione, 3-allyl-1,3,8-triaza-1,7,7,9,9-penta-methyl-spiro[4.5]decane-2,4-dione, 3-glycidyl-1,3,8-triaza-7,7,8,9,9-pentamethyl-spiro[4.5]-decane-2,4-dione, 2-isopropyl-7,7,9,9-tetramethyl-1-oxa-3,8-diaza-4-oxyspiro[4.5]decane, 2-butyl-7,7,9,9-tetramethyl-1-oxa-3,8-diaza-4-oxyspiro [4.5]decane, 2-isopropyl-7,7,9,9-tetramethyl-1-oxa-4,8-diaza-oxyspiro[4.5]decane, 2-butyl-7,7,9,9-tetramethyl-1-oxa-4,8-diaza-3-oxyspiro[4.5]decane, bis[β-(2,2,6,6-tetramethylpiperidino)ethyl]sebacate, α-(2,2,6,6-tetramethylpiperidino)acetic acid n-octyl ester, 1,4-bis(2,2,6,6-tetramethylpiperidino)-2-butene, N-hydroxymethyl-N'-2,2,6,6-tetramethylpiperidin-4-ylurea, N-methoxymethyl-N'-2,2,6,6-tetramethylpiperidin-4-ylurea, N-methoxy-methyl-N'-n-dodecyl-N'-2,2,6,6-tetramethylpiperidin-4-ylurea, O-(2,2,6,6-tetramethylpiperidin-4-yl)-N-methoxymethylurethane.

Phosphites and phosphonates, such as
tris(nonylphenyl)phosphite, tris(2,4-di-tert-butylphenyl) phosphite, bis(2,4-di-tert-butylphenyl)pentaerythritol diphosphite, bis(2,6-di-tert-butyl-4-methylphenyl)pentaerythritol diphosphite, 2,2'-methylenebis(4,6-di-tert-butylphenyl) octyl phosphite, tetrakis(2,4-di-tert-butylphenyl)-[1,1'-biphenyl]-4,4-diylbisphosphonite, 2,2'-ethylidenebis (4,6-di-tert-butylphenyl) fluorophosphite, dioctadecyl pentaerythritol diphosphonate, 2-[[2,4,8,10-tetrakis(1,1-dimethylethyl)dibenzo[d,f][1,3,2]-dioxaphosphin-6-yl]oxy]-N,N-bis[2-[[2,4,8,10-tetrakis(1,1-dimethylethyl)dibenzo[d,f][1,3,2]-dioxaphosphin-6-yl]oxy]ethyl] ethanamine (CAS No. 80410-33-9), bis(2,4-di-tert-butyl-6-methyl-phenyl)ethyl phosphite, 2,4,6-tri-tert-butylphenyl 2-butyl-2-ethyl-1,3-propanediol phosphite, bis(2,4-dicumylphenyl)pentaerythritol diphosphite, hydroxylamines, such as
amines, bis(hydrogenated tallow alkyl), oxidized,
secondary arylamines, such as
N-(2-naphthyl)-N-phenylamine, 2,2,4-trimethyl-1,2-dihydroquinoline polymer (CAS No. 26780-96-1), N-2-propyl-N'-phenyl-p-phenylenediamine, N-(1-naphthyl)-N-phenylamine, (benzenamine, N-phenyl-, reaction products with 2,4,4-trimethylpentene) (CAS No. 68411-46-1), 4-(1-methyl-1-phenylethyl)-N-[4-(1-methyl-1-phenylethyl)phenyl]aniline.

Lactones and benzofuranones, such as
Irganox HP 136 (CAS No. 181314-48-7)
Thioethers and thioesters, such as
distearyl 3,3-thiodipropionate, dilauryl 3,3'-thiodipropionate, ditetradecyl thiodipropionate, di-n-octadecyl disulphide.

UV absorbers, such as
(methanone, [methylenebis(hydroxymethoxyphenylene)]bis[phenyl-), (methanone, [1,6-hexanediyl-bis[oxy(2-hydroxy-4,1-phenylene)]]bis[phenyl-), 2-benzoyl-5-methoxyphenol, 2,4-dihydroxybenzo-phenone, 2,2'-dihydroxy-4-methoxybenzophenone, 2-hydroxy-4-octyloxybenzophenone, 2-hydroxy-4-dodecyloxybenzophenone, 2-(2-hydroxy-4-hexyloxyphenyl)-4,6-diphenyl-1,3,5-triazine, 2,4-bis-(2,4-dimethylphenyl)-6-(2-hydroxy-4-octyloxyphenyl)-1,3,5-triazine, 2-ethoxy-2'-ethyloxalic acid bisanilide, N-(5-tert-butyl-2-ethoxyphenyl)-N'-(2-ethylphenyl)oxamide, dimethyl(p-methoxy-benzylidene)malonate, 2,2'-(1,4-phenylene)bis(3,1-benzoxazin-4-one], N'-(4-ethoxycarbonylphenyl)-N-methyl-N-phenylformamidine, 4-methoxycinnamic acid 2-ethylhexyl ester, 4-methoxycinnamic acid isoamyl ester, 2-phenylbenzimidazole-5-sulphonic acid, 2-cyano-3,3-diphenylacrylic acid 2-ethylhexyl ester, 2-ethylhexyl salicylate, 3-(4-methylbenzylidene)bornan-2-one, chelators, such as
ethylenediaminetetraacetate (EDTA), ethylenediamine, acetylacetone, nitrotiacetic acid, ethylene glycol bis(β-aminoethyl ether)-N,N-tetraacetic acid, 2,2'-bipyridine, 4,4'-dimethyl-2,2'-bipyridine, 2,2',6',2"-terpyridine, 4,4'-diphenyl-2,2'-bipyridine, 2,2'-bipyridine-3,3'-diol, 1,10-phenanthroline, 4-methyl-1,10-phenanthroline, 5-methyl-1,10-phenanthroline, 4,7-dimethyl-1,10-phenanthroline, 5,6-dimethyl-1,10-phenanthroline, 3,4,7,8-tetramethyl-1,10-phenanthroline, 4,7-diphenyl-1,10-phenanthroline, 2,4,7,9-tetramethyl-1,10-phenanthroline, N,N,N',N'-tetramethylethylenediamine, 2-hydroxyquinoline, 8-hydroxyquinoline, 2-hydroxy-4-methylquinaldine, 5-chloro-8-hydroxyquinoline, 5,7-dichloro-8-hydroxyquinoline, 2,4-quinolinediol, 2-quinolinethiol, 8-quinolinethiol, 8-aminoquinoline, 2,2'-biquinoline, 2-quinoxalinol, 3-methyl-2-quinoxalinol, 2,3-dihydroxy-quinoxaline, 2-mercaptopyridine, 2-dimethylaminopyridine, 1,2-bis(dimethylphosphino)ethane, 1,2-bis(diphenylphosphino)ethane, 1,2-bis(diphenylphosphino)propane, 1,4-bis(diphenylphosphino)-butane, polyaspartic acid, iminodisuccinate.

The binder formulations of the invention are especially suitable for use as coating materials, more particularly for use as paint, varnish, primer, impregnating system or stain. Aforementioned uses are likewise provided by the invention.

The binder formulations of the invention comprising transition metal dryers themselves, relative to binder formulations in which the iodine containing compounds, more particularly IPBC, have not been stabilized, do not exhibit any lengthening in the drying time, like that frequently observed when stabilizers are added.

The invention further provides for the use of the biocidal compositions of the invention for protecting industrial materials against destruction or infestation by microorganisms.

The biocidal compositions of the invention are suitable for biocidally treating industrial materials. Industrial materials in the present context are non-living materials which have been prepared for use in industry. The industrial materials are, for example, adhesives, sizes, paper and cardboard, textiles, leather, wood, wood-based materials, coating materials and plastics articles, cooling lubricants and other materials which may be infested or decomposed by microorganisms.

Examples of microorganisms which may bring about degradation or alteration of the industrial materials include bacteria, fungi, yeasts, algae and slime organisms. The active ingredients of the invention act preferably against fungi, more particularly moulds, wood-discolouring and wood-destroying fungi (Basidiomycetes) and also against slime organisms and bacteria.

Microorganisms of the following genera may be mentioned by way of example:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichodemna viride*,
*Escherichia*, such as *Escherichia coli*,
*Pseudomonas*, such as *Pseudomonas aeruginosa*,
*Staphylococcus*, such as *Staphylococcus aureus*.

The invention further provides the industrial materials comprising at least one iodine containing compound having a biocidal action and also a nitrogen containing polymer.

The invention is elucidated below by examples but is not restricted thereto.

EXAMPLES

Example 1

20 g of trimethylolpropane tris[3-(2-methyl-1-aziridinyl) propionate] (Crosslinker CX-100 from DSM) were introduced in 50 ml of water and admixed with 30 g of butyl diglycol while stirring with the magnetic stirrer. This was followed by stirring at 80° C. for 6 hours. A solution was obtained which after cooling was clear and was slightly yellowish.

Determination of Molecular Weight:

25 g of the sample prepared above were freed from water at 50° C. under an oil pump vacuum (about 0.35 mbar). This gave 12.85 g of a highly viscous oil. 1 g of this oil was stirred with 3 times 5 g of THF, and the residue was dried overnight in a desiccator and analyzed by GPC (Standard: polystyrene/PSS Polymer kit). A polymer was identified which had an average molecular weight of 12,238 g/mol. The only component detectable in the THF washing liquid by GC-MS was butyl diglycol.

No aziridine functionalities were detectable.

Example 2

20 g of trimethylolpropane tris[3-(2-methyl-1-aziridinyl) propionate] (Crosslinker CX-100 from DSM) were introduced in 20 ml of water and admixed with 30 g of butyl diglycol while stirring with the magnetic stirrer. This was followed by stirring at 80° C. for 6 hours. A solution was obtained which after cooling was clear and was slightly yellowish.

Refractive index $n_D$=1.4115 (23° C.)

A fraction <50 ppm of the Crosslinker CX-100 starting product was found in this solution by quantitative LC-MS.

Example 3

Production of an Inventive Biocidal Composition 40 g of trimethylolpropane tris[3-(2-methyl-1-aziridinyl) propionate] (Crosslinker CX-100 from DSM) were introduced in 100 ml of water and admixed with 60 g of butyl diglycol while stirring with the magnetic stirrer. This was followed by stirring at 80° C. for 6 hours. A solution was obtained which after cooling was clear and was slightly yellowish. This solution was admixed while stirring with a further 320 g of butyl diglycol and 120 g of IPBC (iodopropargyl butylcarbamate) and the mixture was stirred with a magnetic stirrer for 45 minutes. This gave 640 g of a slightly yellow solution having an IPBC content of 18.8% by weight.

150 g of the solution prepared above was admixed while stirring with 0.3 g of formic acid and the mixture was stirred further for 5 minutes more. The IPBC containing, stabilized biocidal composition was pale yellow and clear.

Refractive index $n_D$=1.4375 (23° C.)

Example 4

Binder Formulations

The compounds/compositions obtained according to Examples 1, 2 and 3 were incorporated in a typical, alkyd resin containing coating system (alkyd stain Affable 1) in the presence of a transition metal dryer (Co) and of a metal oxide pigment (iron oxide). In the case of Examples 1 and 2, containing no IPBC, an IPBC concentrate in Table 2 is additionally added. As a comparative IPBC is incorporated directly (unstabilized IPBC) or as a concentrate in Table 3 (stabilized IPBC according to EP 2236033). The composition of the completed stains can be seen from Table 4. In all of the examples the IPBC concentration in the stains is 0.7%.

TABLE 1

(Formula of alkyd stain A)

| | Ingedients | Amount [% by weight] |
|---|---|---|
| Alkyd stain A | Vialkyd VAF 4349, 80 SD 60, Cytec | 22.5 |
| | Polar solvent Texanol, Eastman | 5.0 |
| | Rheology additive BYK E411, BYK | 0.4 |
| | Shellsol D60, Shell Chemicals | 67.8 |
| | MK-Solcolor red iron oxide 130M (pigment preparation), MK Chemicals | 4.0 |
| | Octa-Soligen ® 69 (containing 6% Co), Borchers | 0.3 |

TABLE 2

IPBC concentrate (unstabilized)

| IPBC | 21% by weight |
|---|---|
| Texanol (2,2,4-trimethyl-1,3-pentanediol monoisobutyrate) | 79% by weight |

TABLE 3

IPBC/aziridine concentrate/comparative

| IPBC | 30% by weight |
|---|---|
| Crosslinker CX-100** | 15% by weight |
| Rhodiasolv DIB* | 55% by weight |

*Mixture consisting of diisobutyl adipate, diisobutyl glutarate, diisobutyl succinate, Rhodia.
**Trimethylolpropane tris[3-(2-methyl-1-aziridinyl)propionate]

The stabilization is determined by performing an accelerated ageing test. For this test the armoured colour system is introduced into tightly closing 200 ml glass bottles, leaving only a minimal remaining amount of air in the vessel, and stored at 40° C. The results can be seen from Table 5.

TABLE 4

Formula of a pigmented, IPBC-armoured alkyd resin containing stain.

| Ingredients | Alkyd stain A-I [%] | Alkyd stain A-II [%] | Alkyd stain A-III [%] | Alkyd stain A-IV [%] Comparative 1 | Alkyd stain A-V [%] Comparative 2 |
|---|---|---|---|---|---|
| Alkyd stain from Table 1 | 95.4 | 95.84 | 96.2 | 99.3 | 97.67 |
| IPBC solution in Texanol (21% IPBC/79% Texanol; Table 1) | 3.42[1)] | 3.27[1)] | — | — | — |

TABLE 4-continued

Formula of a pigmented, IPBC-armoured alkyd resin containing stain.

| Ingredients | Alkyd stain A-I [%] | Alkyd stain A-II [%] | Alkyd stain A-III [%] | Alkyd stain A-IV [%] Comparative 1 | Alkyd stain A-V [%] Comparative 2 |
|---|---|---|---|---|---|
| Stabilizer from Example 1 | 1.18 | — | — | — | — |
| Stabilizer from Example 2 | — | 0.89 | — | — | — |
| Concentrate from Example 3 | — | — | 3.8[1] | — | — |
| IPBC | — | — | — | 0.7[1] | — |
| IPBC/aziridine concentrate (Table 3) | — | — | — | — | 2.33[1] |

[1] Corresponding in each case to 0.7% by weight of IPBC, based on the stain.

TABLE 5

Stability of IPBC in the alkyd stains A (–I) to (–V) at 40° C.

| Alkyd stain | Residual IPBC content [%] based on the starting value | | | |
|---|---|---|---|---|
| | Start | 2 weeks | 4 weeks | 8 weeks |
| A-I | 100 | — | 97 | 94 |
| A-II | 100 | — | 96 | 92 |
| A-III | 100 | — | 98 | 90 |
| A-IV1) | 100 | 96 | 52 | 0 |
| A-V2) | 100 | 100 | 80 | 0 |

1)Unstabilized sample
2)IPBC stabilized with aziridine, without hydrolysis (in accordance with EP 2 236 033 A)

From Table 5 it is clear that the nitrogen containing polymers in relation to the stabilization of IPBC exhibit much higher stability than the unstabilized sample A-IV. A marked improvement is also evident in relation to the IPBC sample stabilized with unreacted aziridine (stain A-V).

What is claimed is:

1. A method for stabilizing iodine containing compounds, the method comprising contacting iodine containing compounds with nitrogen containing polymers obtained by reaction of aziridines in the presence of water, wherein 5% or less of the nitrogen in the nitrogen containing polymers is aziridine nitrogen.

2. The method according to claim 1, wherein the iodine containing compounds are at least one of iodoalkynyl compounds and compounds in which one or more iodine atoms are bonded to one of $sp^2$-hybridized carbon atoms of olefinic double bonds or $sp^3$-hybridized carbon atoms.

3. The method according to claim 2, wherein the iodine containing compounds have biocidal activity and are selected from a group that includes N—($C_1$-$C_{12}$)-alkyl-iodotetrazoles, N—($C_6$-$C_{15}$)-aryl-iodotetrazoles, N—($C_6$-$C_{15}$)-arylalkyl-iodotetrazoles, diiodomethyl p-tolyl sulphone, diiodomethyl p-chlorophenyl sulphone, 3-bromo-2,3-diiodo-2-propenyl alcohol, 2,3,3-triiodoallyl alcohol, 4-chloro-2-(2-chloro-2-methylpropyl)-5-[(6-iodo-3-pyridinyl)methoxy]-3 (2H)-pyridazinone (CAS RN: 120955-77-3), iodofenphos, 3-iodo-2-propynyl 2,4,5-trichlorophenyl ether, 3-iodo-2-propynyl 4-chlorophenyl formal (IPCF), N-iodopropargyloxycarbonyl-alanine, N-iodopropargyloxycarbonyl-alanine ethyl ester, 3-(3-iodopropargyl)benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl) hexyl dicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl-carbamic ester (IPC), 3-bromo-2,3-diiodo-2-propenyl ethylcarbamate, 3-iodo-2-propynyl n-hexylcarbamate and 3-iodo-2-propynyl cyclohexylcarbamate.

4. The method according to claim 1 wherein the nitrogen containing polymers have a weight-average molecular weight of more than 1000 g/mol.

5. The method according to claim 1 wherein the nitrogen containing polymers have a nitrogen content of 1% to 20% by weight.

6. The method according to claim 1 wherein the nitrogen containing polymers are polymers possessing at least one beta-aminoamine function.

7. The method according to claim 1, wherein the nitrogen containing polymers have a weight-average molecular weight of 3000 to 60,000 g/mol, a nitrogen content of 5% to 12% by weight, and two or more beta-aminoamine functions.

8. The method according to claim 1, wherein the aziridines are aziridine compounds of the formula (I)

(I)

where
R[1] is hydrogen, alkyl or cycloalkyl, each of which is unsubstituted or substituted and/or mono- or polyethylenically unsaturated, or in each case substituted or unsubstituted fullerenyl, aryl, alkoxy, alkoxycarbonyl, arylcarbonyl or alkanoyl,
R[2], R[3], R[4] and R[5] independently of one another are the compounds as defined by R[1], halogen, hydroxyl, carboxyl, alkylsulphonyl, arylsulphonyl, nitrile, or isonitrile, or R[2] and R[4], or R[3] and R[5], together with the carbon atoms to which they are attached, form a 5- to 10-membered carbocyclic ring which is unsubstituted or substituted and/or mono- or polyethylenically unsaturated.

9. Biocidal compositions comprising:
a) at least one iodine containing compound having biocidal action; and
b) at least one nitrogen containing polymer obtained by reaction of aziridines in the presence of water, wherein 5% or less of the nitrogen in the nitrogen containing polymers is aziridine nitrogen.

10. The biocidal composition according to claim 9, wherein the nitrogen containing polymers have a weight-average molecular weight of more than 1000 g/mol, a nitrogen content of 1% to 20% by weight, and at least one beta-aminoamine function.

11. The biocidal composition according to claim 9, further comprising acid.

12. The biocidal composition according to claim 9, further comprising active ingredients selected from a group that includes antimicrobially active compounds, fungicides, bactericides, herbicides and insecticides.

13. A binder formulation comprising:
a) at least one binder,
b) at least one iodine containing compound with biocidal action, and
c) at least one nitrogen containing polymer obtained by reaction of aziridines in the presence of water, wherein 5% or less of the nitrogen in the nitrogen containing polymers is aziridine nitrogen.

14. The binder formulation according to claim 13, wherein the nitrogen containing polymers have a weight-average molecular weight of more than 1000 g/mol, a nitrogen content of 1% to 20% by weight, and at least one beta-aminoamine function.

15. The binder formulation according to claim 13, further comprising at least one transition metal dryer.

16. A method for protecting industrial materials against destruction or infestation by microorganisms, the method comprising contacting the industrial materials with the biocidal compositions according to claim 9.

17. The method according to claim 8, wherein:
the iodine containing compounds have biocidal activity and are selected from a group that includes N—($C_1$-$C_{12}$)-alkyl-iodotetrazoles, N—($C_6$-$C_{15}$)-aryl-iodotetrazoles, N—($C_6$-$C_{15}$)-arylalkyl-iodotetrazoles, diiodomethyl p-tolyl sulphone, diiodomethyl p-chlorophenyl sulphone, 3-bromo-2,3-diiodo-2-propenyl alcohol, 2,3,3-triiodoallyl alcohol, 4-chloro-2-(2-chloro-2-methyl-propyl)-5-[(6-iodo-3-pyridinyl)methoxy]-3(2H)-pyridazinone (CAS RN: 120955-77-3), iodofenphos, 3-iodo-2-propynyl 2,4,5-trichlorophenyl ether, 3-iodo-2-propynyl 4-chlorophenyl formal (IPCF), N-iodopropargyloxycarbonyl-alanine, N-iodopropargyloxycarbonyl-alanine ethyl ester, 3-(3-iodopropargyl)benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl)hexyl dicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl-carbamic ester (IPC), 3-bromo-2,3-diiodo-2-propenyl ethylcarbamate, 3-iodo-2-propynyl n-hexyl-carbamate, and 3-iodo-2-propynyl cyclohexylcarbamate;
the nitrogen containing polymers have a weight-average molecular weight of more than 1000 g/mol, a nitrogen content of 1% to 20% by weight, and at least one, beta-aminoamine function; and
the nitrogen containing polymers contain no detectable amounts of aziridine rings.

* * * * *